United States Patent
Eichler et al.

(10) Patent No.: US 9,724,166 B2
(45) Date of Patent: *Aug. 8, 2017

(54) MEDICAL DEVICE NAVIGATION SYSTEM

(71) Applicant: MediGuide Ltd., Haifa (IL)

(72) Inventors: Uzi Eichler, Haifa (IL); Alon Izmirli, Ganot Hadar (IL); Yuval Vaknin, Hanaton (IL); Adi Raveh, Givat-Ada (IL)

(73) Assignee: MEDIGUIDE LTD., Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/090,368

(22) Filed: Apr. 4, 2016

(65) Prior Publication Data

US 2016/0287343 A1    Oct. 6, 2016

Related U.S. Application Data

(63) Continuation of application No. 14/208,120, filed on Mar. 13, 2014, now Pat. No. 9,326,702.
(Continued)

(51) Int. Cl.
*A61B 5/05*    (2006.01)
*A61B 34/20*    (2016.01)
(Continued)

(52) U.S. Cl.
CPC .............. *A61B 34/20* (2016.02); *A61B 5/042* (2013.01); *A61B 5/062* (2013.01); *A61B 6/00* (2013.01);
(Continued)

(58) Field of Classification Search
CPC ....... A61B 5/05; A61B 19/52; A61B 19/5244; A61B 5/06; A61B 2019/5238; A61B 2019/5251
See application file for complete search history.

(56) References Cited

U.S. PATENT DOCUMENTS

| | | |
|---|---|---|
| 4,593,189 A | 6/1986 | Stoub |
| 5,072,121 A | 12/1991 | Jazbec |
| | (Continued) | |

FOREIGN PATENT DOCUMENTS

| | | |
|---|---|---|
| EP | 1942662 A1 | 7/2008 |
| WO | 2005013828 | 2/2005 |
| | (Continued) | |

OTHER PUBLICATIONS

Linear X-Ray Photodiode Detector Array with Signal Amplification, X_SCAN Imaging Corporation, XB8816 Series, Apr. 2010, Rev. 1.3, 8 pages.

*Primary Examiner* — Joel Lamprecht
(74) *Attorney, Agent, or Firm* — Dykema Gossett PLLC

(57) ABSTRACT

A system for navigating a medical device is provided. In one embodiment, a magnetic field generator assembly generates a magnetic field. Position sensors on the medical device, on an imaging system and on the body generate signals indicative of the positions within the magnetic field. The generator assembly and reference sensors are arranged such that a correlation exists between them and the positions of the body and of a radiation emitter and a radiation detector of the imaging system. An electronic control unit (ECU) determines, responsive to signals generated by the sensors, a position of the medical device, a position of one of the radiation emitter and detector and a distance between the emitter and detector. Using this information, the ECU can, for example, register images from the imaging system in a coordinate system and superimpose an image of the device on the image from the imaging system.

15 Claims, 8 Drawing Sheets

Related U.S. Application Data

(60) Provisional application No. 61/787,542, filed on Mar. 15, 2013, provisional application No. 61/834,223, filed on Jun. 12, 2013.

(51) Int. Cl.
  *A61B 5/06* (2006.01)
  *A61B 6/00* (2006.01)
  *A61B 18/14* (2006.01)
  *A61B 6/10* (2006.01)
  *A61B 5/042* (2006.01)
  *A61B 90/00* (2016.01)

(52) U.S. Cl.
  CPC ............ *A61B 6/102* (2013.01); *A61B 6/4441* (2013.01); *A61B 6/527* (2013.01); *A61B 6/54* (2013.01); *A61B 6/547* (2013.01); *A61B 6/586* (2013.01); *A61B 6/589* (2013.01); *A61B 18/1492* (2013.01); *A61B 90/37* (2016.02); *A61B 6/5258* (2013.01); *A61B 6/545* (2013.01); *A61B 2034/2051* (2016.02); *A61B 2090/365* (2016.02); *A61B 2090/376* (2016.02); *A61B 2090/3764* (2016.02)

(56) References Cited

U.S. PATENT DOCUMENTS

| | | |
|---|---|---|
| 5,391,199 A | 2/1995 | Ben-Haim |
| 5,443,489 A | 8/1995 | Ben-Haim |
| 5,558,091 A | 9/1996 | Acker et al. |
| 5,828,221 A | 10/1998 | Habraken et al. |
| 6,233,476 B1 | 5/2001 | Strommer et al. |
| 6,408,051 B2 | 6/2002 | Habraken et al. |
| 6,498,944 B1 | 12/2002 | Ben-Haim et al. |
| 6,507,751 B2 | 1/2003 | Blume et al. |
| 6,558,333 B2 | 5/2003 | Gilboa et al. |
| 6,690,963 B2 | 2/2004 | Ben-Haim et al. |
| 6,788,967 B2 | 9/2004 | Ben-Haim et al. |
| 7,172,340 B2 | 2/2007 | Oota |
| 7,197,354 B2 | 3/2007 | Sobe |
| 7,263,397 B2 | 8/2007 | Hauck et al. |
| 7,386,339 B2 | 6/2008 | Strommer et al. |
| 7,531,807 B2 | 5/2009 | Hefetz |
| 7,693,263 B2 | 4/2010 | Bouvier et al. |
| 7,697,973 B2 | 4/2010 | Strommer et al. |
| 8,269,176 B2 | 9/2012 | D'Ambrosio et al. |
| 9,326,702 B2 * | 5/2016 | Eichler .................. A61B 6/102 |
| 2006/0115054 A1 | 6/2006 | Yatsenko et al. |
| 2007/0016006 A1 | 1/2007 | Shachar |
| 2008/0118103 A1 | 5/2008 | Pescatore et al. |
| 2008/0125997 A1 | 5/2008 | Li et al. |
| 2008/0183071 A1 | 7/2008 | Strommer et al. |
| 2008/0269588 A1 | 10/2008 | Csavoy |
| 2009/0247942 A1 | 10/2009 | Kirschenman |
| 2009/0247944 A1 | 10/2009 | Kirschenman et al. |
| 2009/0247993 A1 | 10/2009 | Kirschenman et al. |
| 2009/0248042 A1 | 10/2009 | Kirschenman |
| 2010/0256558 A1 | 10/2010 | Olson et al. |
| 2011/0015569 A1 | 1/2011 | Kirschenman et al. |
| 2012/0230473 A1 | 9/2012 | Stagnitto |
| 2013/0158476 A1 | 6/2013 | Olson |

FOREIGN PATENT DOCUMENTS

| | | |
|---|---|---|
| WO | 2009120982 A2 | 10/2009 |
| WO | 2010078453 A1 | 7/2010 |
| WO | 2012090148 A1 | 7/2012 |

\* cited by examiner

MEDICAL DEVICE NAVIGATION SYSTEM

CROSS-REFERENCE TO RELATED APPLICATIONS

This application is a continuation of U.S. application Ser. No. 14/208,120, filed 13 Mar. 2014 (the '120 application), now U.S. Pat. No. 9,326,702, which claims the benefit of both U.S. provisional patent application No. 61/834,223, filed Jun. 12, 2013 (the '223 application), and U.S. provisional patent application No. 61/787,542, filed Mar. 15, 2013 (the '542 application). The '120 application, the '223 application, and the '542 application are all hereby incorporated by reference in their entirety as though fully set forth herein.

BACKGROUND a. Field

The present disclosure relates to a system for navigating a medical device within a body. In particular, the instant disclosure relates to a medical device navigation system configured to obtain information from and/or interact with a medical imaging system when the medical imaging system is not integrated with the medical device navigation system.

b. Background

A wide variety of medical devices are inserted into the body to diagnose and treat various medical conditions. Catheters, for example, are used to perform a variety of tasks within human bodies and other bodies including the delivery of medicine and fluids, the removal of bodily fluids and the transport of surgical tools and instruments. In the diagnosis and treatment of atrial fibrillation, for example, catheters may be used to deliver electrodes to the heart for electrophysiological mapping of the surface of the heart and to deliver ablative energy to the surface among other tasks. Catheters are typically routed to a region of interest through the body's vascular system. In a conventional approach, an introducer is used to puncture the skin surface and a sheath having an inner diameter greater than the outer diameter of the catheter is threaded through the vasculature to a region of interest. The catheter is then moved longitudinally through the sheath to the region of interest either manually by a clinician or through the use of electromechanical drive systems.

It is desirable to track the position of medical devices such as catheters as they are moved within the body so that, for example, drugs and other forms of treatment are administered at the proper location and medical procedures can be completed more efficiently and safely. One conventional means to track the position of medical devices within the body is fluoroscopic imaging. Fluoroscopy is disadvantageous, however, because it subjects the patient and physician to undesirable levels of electromagnetic radiation. As a result, medical device navigation systems have been developed to track the position of medical devices within the body. These systems typically rely on the generation of electrical or magnetic fields and the detection of induced voltages and currents on position sensors attached to the medical device and/or external to the body. The information derived from these systems is then provided to a physician through, for example, a visual display. Oftentimes, a representation of the medical device is displayed relative to a computer model or one or more images (including, but not limited to, fluoroscopic images) of the anatomical region in which the device is being maneuvered. In order to display the medical device at the correct location relative to the model or image, the model or image must be registered within the coordinate system of the navigation system.

Images may be registered in the coordinate system of a medical device navigation system in a variety of ways. If the imaging system used to capture the images is physically integrated with the navigation system, as described in commonly assigned U.S. Published Patent Application No. 2008/0183071, the entire disclosure of which is incorporated herein by reference, the imaging system can be registered with the navigation system during installation and the spatial relationship of the navigation system to the imaging system is thereafter constant and known, obviating the need for registration during each new procedure. Where the navigation system and imaging system are physically separate, however, the changing spatial relationship of the systems makes registration more complicated. Further, even when the navigation system and imaging system are physically integrated, the initial registration process is relatively time consuming.

The foregoing discussion is intended only to illustrate the present field and should not be taken as a disavowal of claim scope.

BRIEF SUMMARY

The present disclosure relates to a medical device navigation system. In particular, the instant disclosure relates to a medical device navigation system configured to obtain information from a medical imaging system when the medical imaging system is not integrated with the medical device navigation system. In various embodiments, the information may include, for example, image data for use in generating images captured by the imaging system, information regarding an operational characteristics of the imaging system such as the time images were capture, the amount of radiation emitted by the system, or the mode of operation (e.g. capturing individual images or a cine loop), or information regarding the geometry of the imaging system and its components. Also in various embodiments, the information may be used by the medical device navigation system to, for example, register images generated by the imaging system in the coordinate system of the medical device navigation system, display the information to a user, or detect interference between the imaging and medical device navigation systems. In various embodiments, the information may be obtained by the medical device navigation system by sensing mechanical motion of a component of the imaging system or relative mechanical motion between components of the imaging system, capturing inputs to and outputs from the imaging system including signals from a control pedal or image data output by the imaging system, or by sensing operation of the system such as generation of radiation.

A system for navigating a medical device relative to a body in accordance with one embodiment of the present teachings includes a magnetic field generator assembly configured to generate a magnetic field. The medical device includes a device position sensor configured to generate a device position signal responsive to a position of the device position sensor within the magnetic field. The system further includes first and second reference position sensors. The first reference position sensor is configured to be affixed to an imaging system of a type comprising a structure movable relative to the body and comprising an arm, a radiation emitter coupled to the arm and a radiation detector coupled to the arm and movable relative to the arm. The second reference position sensor is configured to be affixed to the imaging system or the body. The first and second reference position sensors generate first and second reference position signals, respectively, responsive to positions of the first and second reference position sensors within the magnetic field. A position of a first member of the magnetic field generator assembly, the first reference position sensor and the second reference position sensor is correlated to a position of the radiation emitter. A position of a second member of the magnetic field generator assembly, the first reference position sensor and the second reference position sensor is correlated to a position of the radiation detector. A position of a third member of the magnetic field generator assembly, the first reference position sensor and the second reference position sensor is correlated to a position of the body. An electronic control unit is configured to, responsive to the device position signal and the first and second reference position signals, determine a device position of the medical device within a first coordinate system, a reference position of one of the radiation detector and the radiation emitter within the first coordinate system and a distance between the radiation detector and the radiation emitter.

A system for navigating a medical device relative to a body in accordance with another embodiment of the present teachings includes an electronic control unit configured to receive a device position signal from a device position sensor disposed on the medical device. The device position sensor generates the device position signal responsive to a position of the device position sensor within a magnetic field generated by a magnetic field generator assembly. The electronic control unit is further configured to receive first and second reference position signal from a first position sensor and a second position sensor, respectively. The first reference position sensor is configured to be affixed to an imaging system of a type comprising a structure movable relative to the body and comprising an arm, a radiation emitter coupled to the arm and a radiation detector coupled to the arm and movable relative to the arm. The second reference position sensor is configured to be affixed to the imaging system or the body. The first and second reference position signals are responsive to positions of the first and second reference position sensors within the magnetic field wherein a position of a first member of the magnetic field generator assembly, the first reference position sensor and the second reference position sensor is correlated to a position of the radiation emitter, a position of a second member of the magnetic field generator assembly, the first reference position sensor and the second reference position sensor is correlated to a position of the radiation detector and a position of a third member of the magnetic field generator assembly, the first reference position sensor and the second reference position sensor is correlated to a position of the body. The electronic control unit is further configured to determine, responsive to the device position signal and the first and second reference position signals, a device position of the medical device within a first coordinate system; a reference position of one of the radiation detector and the radiation emitter within the first coordinate system; and, a distance between the radiation detector and the radiation emitter.

A system for navigating a medical device relative to a body in accordance with another embodiment of the present teachings includes a magnetic field generator assembly configured to generate a magnetic field. The medical device comprises a device position sensor configured to generate a device position signal responsive to a position of the device position sensor within the magnetic field. The magnetic field generator assembly is configured to passively engage an anti-collision feature of an imaging system.

The foregoing and other aspects, features, details, utilities, and advantages of the present disclosure will be apparent from reading the following description and claims, and from reviewing the accompanying drawings.

DETAILED DESCRIPTION

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
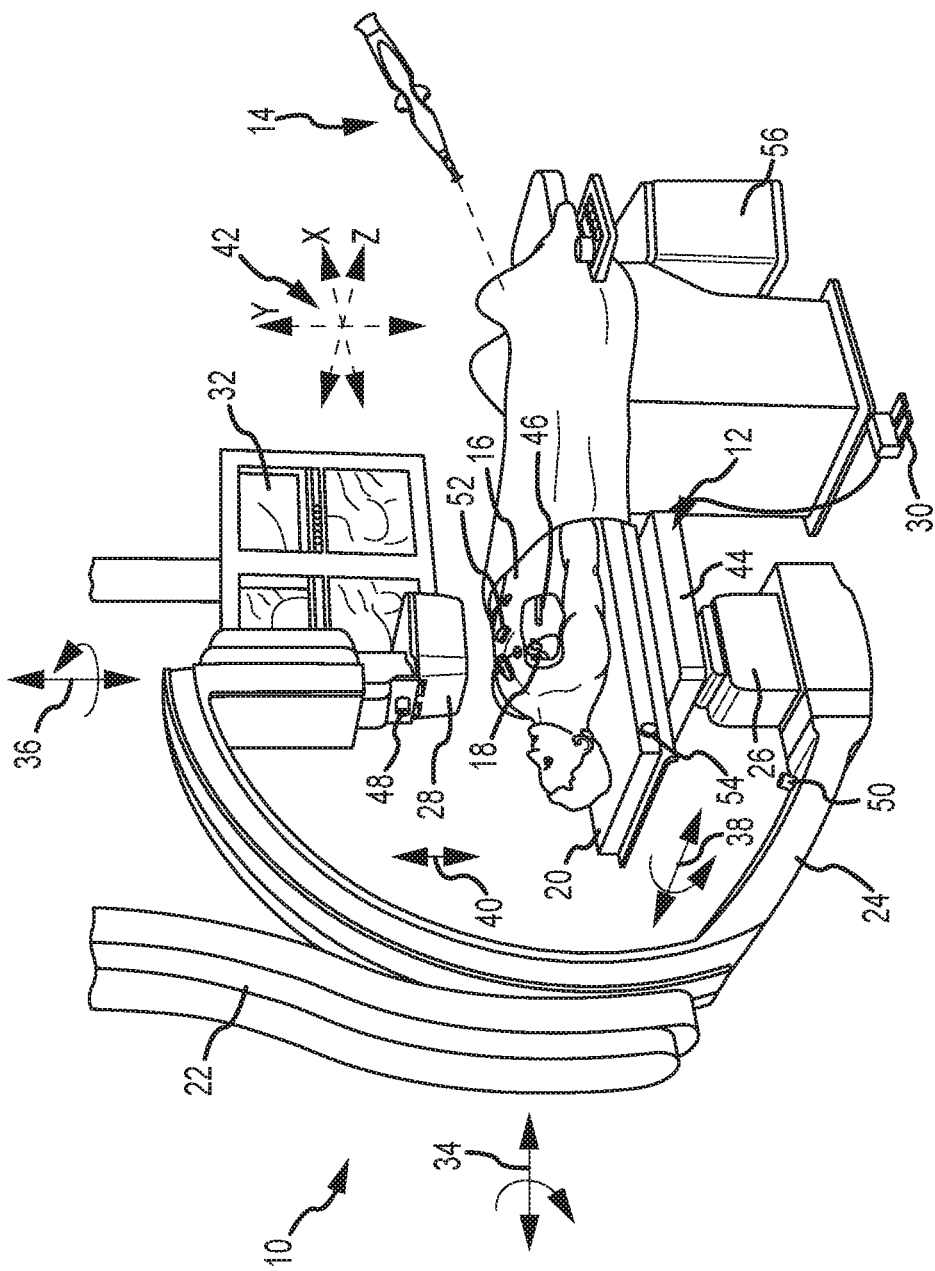
FIG. 1 is a diagrammatic view of a medical device navigation system in accordance with one embodiment of the present teachings.

Referring now to the drawings wherein like reference numerals are used to identify identical components in the various views, FIG. 1 illustrates an electrophysiology lab including an imaging system 10 and a system 12 for navigating a medical device 14 relative to and within a region of interest in a body 16 such as the heart 18 in accordance with one embodiment of the present teachings. Device 14 may comprise, for example, an electrophysiological (EP) mapping catheter, an intracardiac echocardiography (ICE) catheter or an ablation catheter used to diagnose and treat cardiac tissue. It should be understood, however, that the inventive system could be used to navigate a variety of diagnostic and treatment devices used to treat various regions of interest within body 16.

Imaging system 10 is provided to acquire images of heart 18 or another anatomical regions of interest and comprises a fluoroscopic imaging system in the illustrated embodiment. System 10 has a structure that is movable relative to the various components of system 12 and relative to body 16 and a table 20 supporting body 16. System 10 may include a number of structural components including, in the illustrated embodiment, a support 22, an arm 24, a radiation emitter 26 and a radiation detector 28. System 10 may also include an electronic control unit (not shown) for controlling operation of system 10 and one or more input devices such as control pedal 30 and output devices such as display 32.

Support 22 provides a means for supporting arm 24 and for moving arm 24, emitter 26 and detector 28 relative to body 16. In the illustrated embodiment, support 22 is suspended from a ceiling in the EP lab. Support 22 may be affixed to rails (not shown) or similar structures and may be moved by mechanical, electrical, or electromechanical devices (not shown). Support 22 may be configured to rotate with arm 24, emitter 26 and detector 28 about an axis 34 to position arm 24, emitter 26 and detector 28 relative to body 16.

Arm 24 provides a means for supporting emitter 26 and detector 28 relative to body 16. Arm 24 may be substantially C-shaped (i.e., a "C-arm") to provide sufficient clearance relative to body 16 and table 20. Arm 24 is configured to rotate in either direction about an axis 36 relative to support 22 to cause corresponding movement of emitter 26 and detector 28 and position emitter 26 and detector 28 relative to body 16 to permit images to be acquired from a variety of angles or orientations.

Emitter 26 is provided to emit electromagnetic radiation (e.g., X-rays) over a field of view between emitter 26 and detector 28 including the anatomical region of interest in body 16. Emitter 26 is disposed at one end of arm 24.

Detector 28 captures electromagnetic radiation passing through the anatomical region of interest in body 16 and generates signals used to create images of the region of interest. In one embodiment, detector 28 may comprise a flat detector and may be configured to rotate about an axis 38 relative to arm 24 and may also be movable relative to arm 24 along an axis 40 to vary the distance between the emitter 26 and detector 28 (i.e. the "source to image" distance or "SID"). Detector 28 is disposed at an opposite end of arm 24 relative to emitter 26.

The relative movement of imaging system 10 and other objects within the electrophysiology lab create various degrees of freedom that system 12 may need to account for when navigating device 14. In addition to rotation about axes 34, 36, 38 and movement along axes 40, table 20 may move relative to imaging system 10 (or vice versa) in either direction along three orthogonal axes resulting in as many as seven degrees of freedom.

Control pedal 30 provides a means for the physician to control imaging system 12. The physician may, for example, depress pedal 30 to activate radiation emitter 26. Pedal 30 may communicate with an electronic control unit (not shown) for imaging system 12 via a wired or wireless connection.

Display 32 is provided to convey information to a physician to assist in diagnosis and treatment. Display 32 may comprise one or more computer monitors or other display devices. Display 32 may present a graphical user interface (GUI) to the physician. The GUI may include a variety of information including, for example, an image of the geometry of heart 18, electrophysiology data associated with the heart 18, graphs illustrating voltage levels over time for various electrodes on medical device 14, and images of medical device 14 and related information indicative of the position of device 14 and other devices relative to the heart 18.

System 12 may be used to determine the position of device 14 within body 16 and within a coordinate system 42 and to navigate device 14 within body 16. System 12 may also be used to determine the positions of other movable objects within the EP lab within coordinate system 42 including body 16 and table 20. In accordance with one embodiment of the present teachings, system 12 is also used to determine the position of imaging system 10 within coordinate system 42 and, in particular, various components of imaging system 10. System 12 employs magnetic fields and may comprise the system made available under the trademark MediGuide™ by St. Jude Medical, Inc. and generally shown and described in, for example, U.S. Pat. No. 7,386,339, the entire disclosure of which is incorporated herein by reference. System 12 may include a magnetic field generator assembly 44, means, such as position sensors 46, 48, 50, 52, 54 for generating information regarding the position of device 14 within body 16 and the position of various objects in the EP lab such as imaging system 10, body 16 and table 20. System 12 may also include an electronic control unit (ECU) 56 and a display such as display 32.

Figure 2:
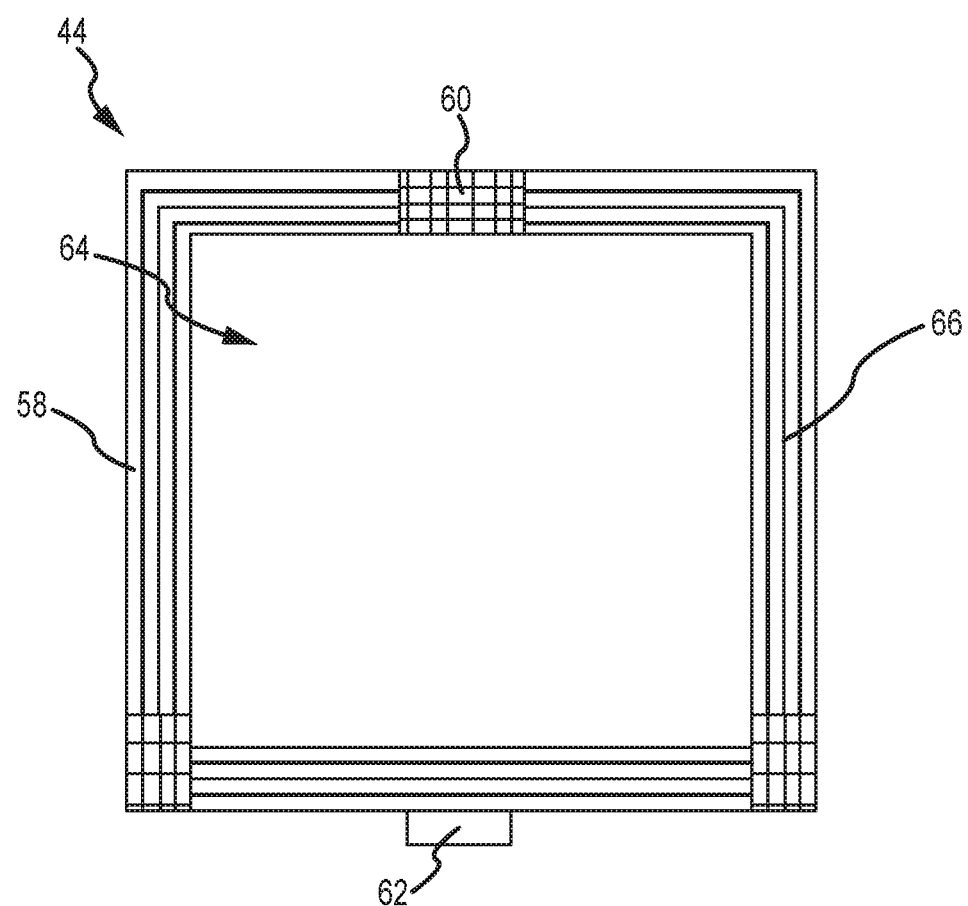
FIG. 2 is a diagrammatic view of a magnetic field generator assembly of the system of FIG. 1.

Generator assembly 44 generates magnetic fields that cause a response in sensors 46, 48, 50, 52, 54 indicative of the location and orientation of sensors 46, 48, 50, 52, 54 within the magnetic fields and within coordinate system 42. Referring to FIG. 2, generator assembly 44 may include a housing 58, a plurality of field generators 60, and a control interface 62.

Figure 3:
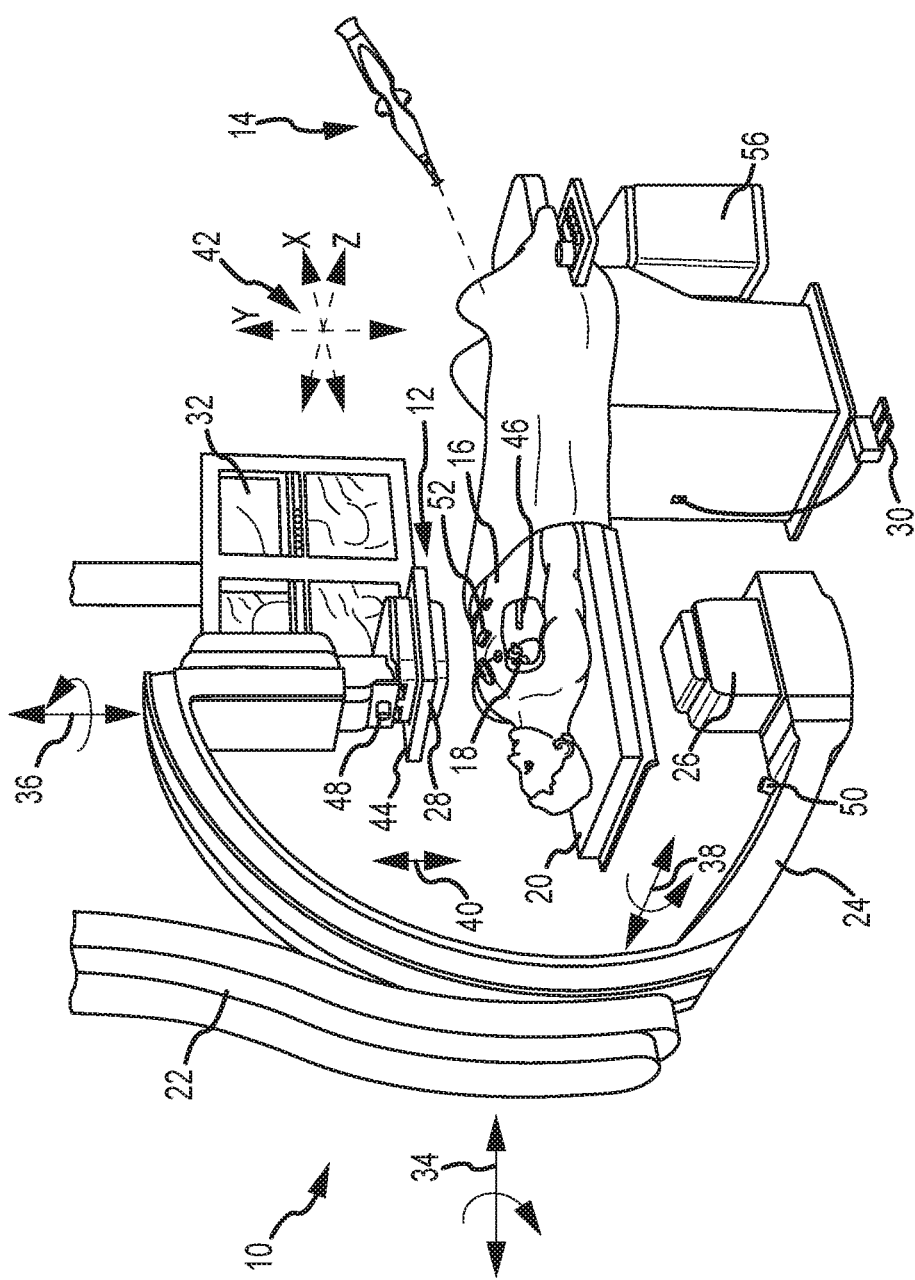
FIG. 3 is a diagrammatic view of a medical device navigation system in accordance with another embodiment of the present teachings.
Figure 4:
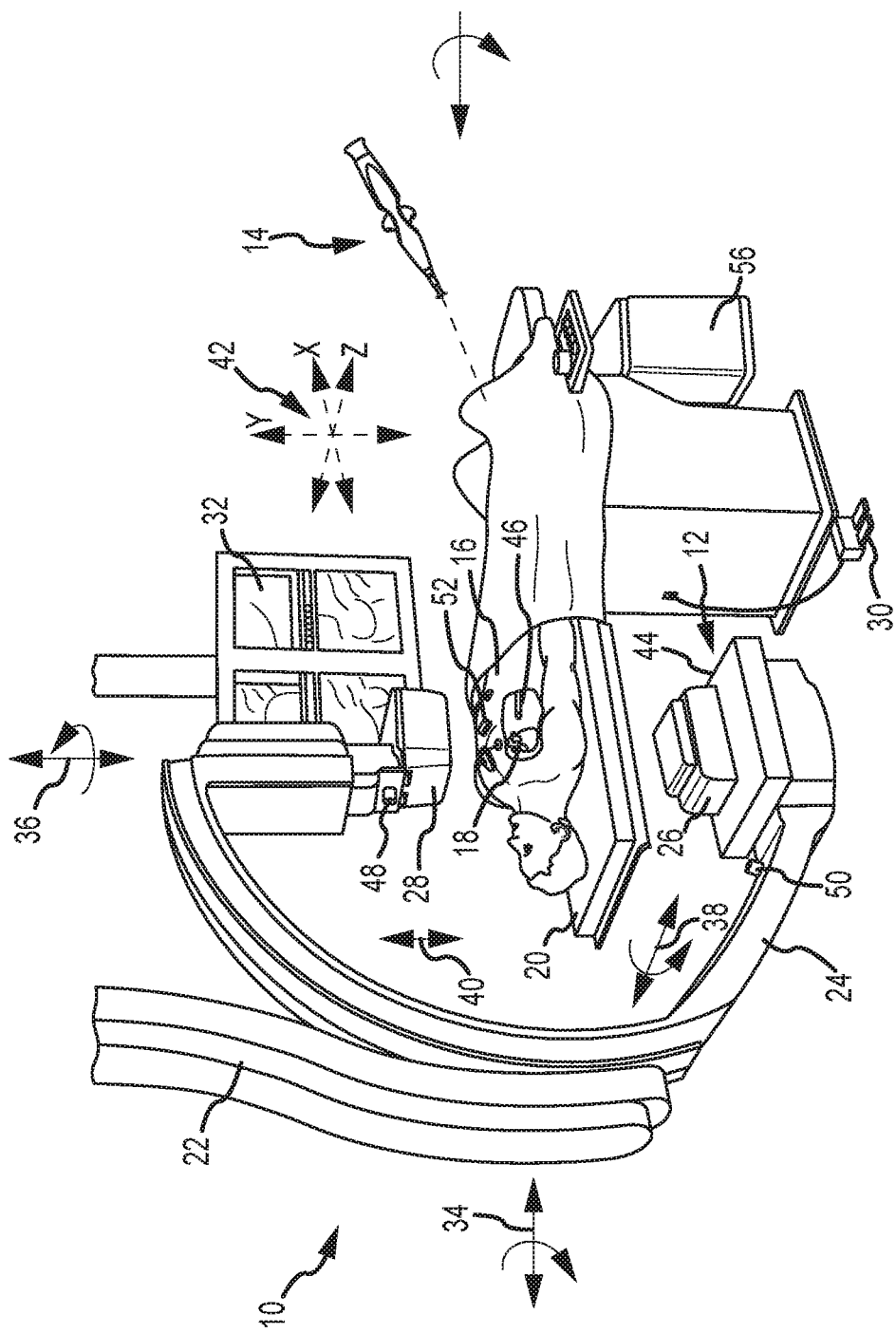
FIG. 4 is a diagrammatic view of a medical device navigation system in accordance with another embodiment of the present teachings.

Housing 58 provides structural support to other components of assembly 44 including field generators 60, associated conductors, and possibly control and signal processing circuitry and protects these components from foreign objects and elements. In certain embodiments, housing 58 may be mounted to a component of imaging system 10 such as arm 24, emitter 26 or detector 28. Referring to FIGS. 3 and 4, for example, assembly 44 may be mounted to detector 28 and to emitter 26 in certain embodiments. Referring again to FIG. 1, in accordance with one embodiment, housing 58 is not directly coupled to, or integrated with, imaging system 10. As a result, generator assembly 44 may be used with various imaging systems, but is not co-registered with imaging system 10. In accordance with one embodiment, housing 58 may be disposed underneath table 20 and body 16 and may be configured to be attached to table 20. Referring again to FIG. 2, housing 58 may be substantially square in shape and may have a central aperture 64 through which the field of view from emitter 26 to detector 28 may extend.

Field generators 60 generate one or more magnetic fields. Field generators 60 may be disposed within housing 58 and spaced apart from one another. Each generator may have three orthogonally arranged coils, arranged to create magnetic fields within an area including body 16 and to control the strength, orientation, and frequency of the fields. Magnetic fields are generated by the coils and current or voltage measurements for one or more position sensors 46, 48, 50, 52, 54 are obtained. The measured currents or voltages are proportional to the distance of the sensors 46, 48, 50, 52, 54 from the coils thereby allowing determination of a position of the sensors 46, 48, 50, 52, 54 within coordinate system 42.

Interface 62 provides a means for connecting assembly 44 to ECU 56. In particular, interface 62 provides an electromechanical connection point to connect cables and other conductors external to assembly 44 (such as those extending between assembly 44 and ECU 56) with conductors internal to housing 58 (such as those extending between interface 62 and field generators 60). In accordance with one aspect of the present teachings, one or more printed circuit boards 66 having conductive traces furnish the conductors internal to housing 58 and the printed circuit board 66 is relatively thin, having conductors with a thickness (e.g., 0.1 millimeter) such that board 66 is translucent and therefore will minimize potential interference with imaging system 10.

Position sensors 46, 48, 50, 52, 54 provide a means for generating information regarding the position of various objects within coordinate system 42. As sensors 46, 48, 50, 52, 54 move within the magnetic field generated by generator assembly 44, the current output of each sensor 46, 48, 50, 52, 54 changes thereby indicating the location of sensors 46, 48, 50, 52, 54 within the magnetic field and within coordinate system 42. Position sensors 46, 48, 50, 52, 54 may comprise coils. Sensor 46, for example, may be wound about device 14 at or near distal end of device 14, embedded within a wall of device 14 or within a cavity within device 14. Sensors 46, 48, 50, 52, 54 may also have appropriate insulation and/or shielding (e.g., a conductive foil or wire mesh) to cancel potential interferences from other devices near body 16. In alternative embodiments, sensors 46, 48, 50, 52, 54 may comprise any position sensors for detecting changes in magnetic fields including, for example, Hall effect sensors, magnetoresistive sensors and sensors made from magnetoresistive materials and piezoelectric materials and the like. Sensors 46, 48, 50, 52, 54 may also be of a type that is able to sense position in one or more (e.g. 1 to 6) degrees of freedom relative to a field generator. Sensors 46, 48, 50, 52, 54 may communicate position signals to ECU 56 through an interface (not shown) using wires or other conductors or wirelessly.

In accordance with one embodiment of the present teachings, position sensors 48, 50 provides a means for generating information regarding the position of imaging system 10 within coordinate system 42. Position sensors 48, 50 are affixed to components of imaging system 10. In the illustrated embodiment, sensor 48 is configured to be affixed to radiation detector 28 while sensor 50 is configured to be affixed to a component of imaging system 10 other than detector 28. Sensor 50 may, for example, be affixed to any of support 22, arm 24 or radiation emitter 26 and is affixed to emitter 26 in the illustrated embodiment. Signals generated by sensor 48 are indicative of the position of radiation detector 28 within coordinate system 42, but also can be used to determine the position of detector 28 relative to other components of imaging system 10 including, for example, the distance between emitter 26 and detector 28. Signals generated by sensor 50 are indicative of the position of the component to which sensor 50 is attached within coordinate system 42 and, in particular, the angle orientation of arm 24, emitter 26 and detector 28.

Figure 5:
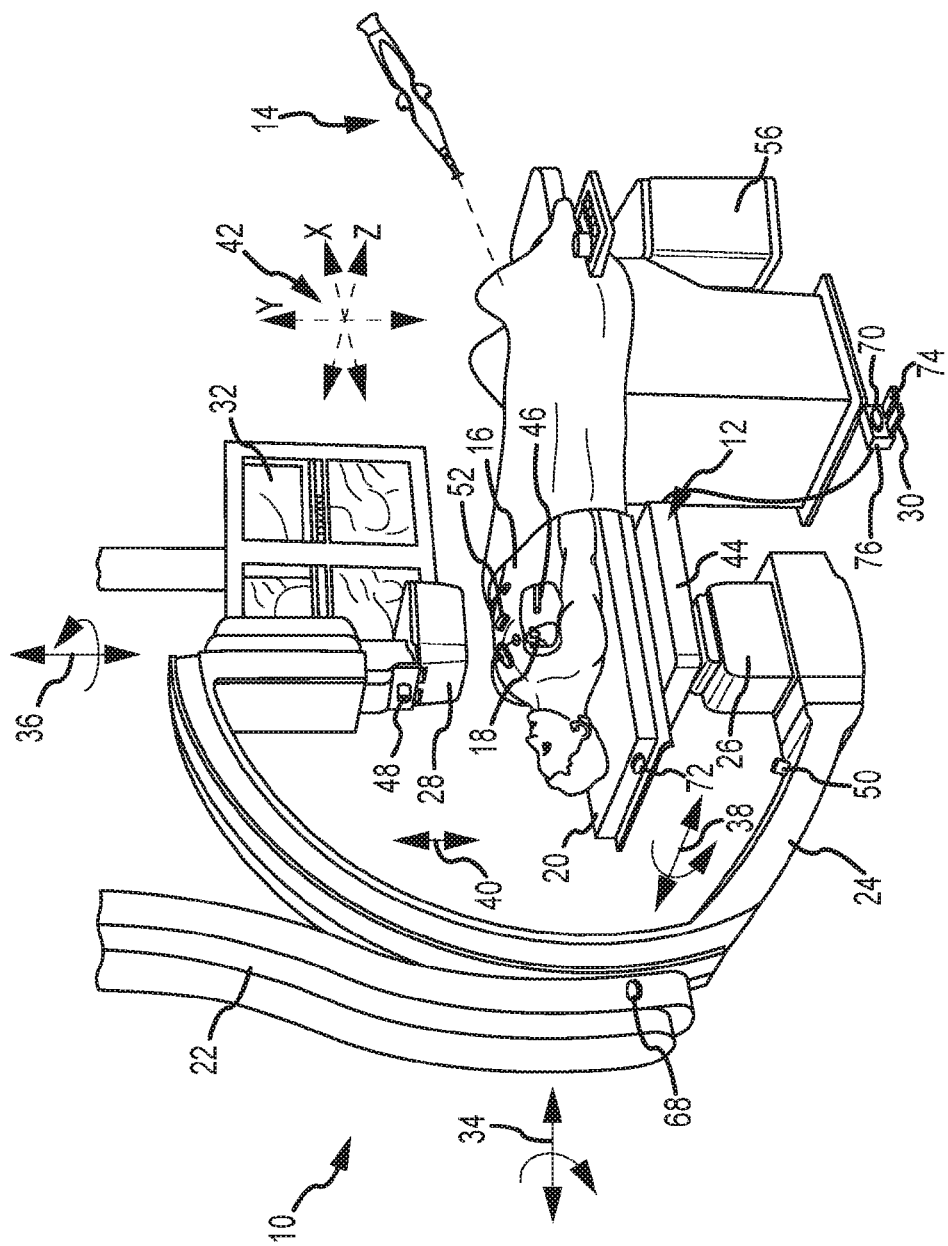
FIG. 5 is a diagrammatic view of a medical device navigation system in accordance with another embodiment of the present teachings.

In accordance with other embodiments of the present teachings, information regarding the position of imaging system 10 may be generated other than through sensors 48, 50. Referring to FIG. 5, in another embodiment one or more motion sensors 68, 70, 72 may generate signals indicative of the movement of one component of imaging system 10 relative to either a prior position of the component or relative to another component of imaging system 10. Motion sensors 68, 70, 72 may, for example, comprise accelerometers, inclinometers or gyroscopes that provide an indication of the change in position of imaging system 10. Alternatively sensors 68, 70, 72 may comprise, for example, infrared or ultrasound sensors or linear or rotary variable differential transformers that provide an indication of the change in position of imaging system 10 relative to another component of imaging system 10 or another frame of reference. In the illustrated embodiment, for example, motion sensor 68 may generate a signal indicative of the degree of rotation of arm 24 relative to support 22. Motion sensor 70 may generate a signal indicative of the degree of separation between pedal 74 and a base 76 in control pedal 30. Alternatively, motion sensor 70 may comprise a pressure switch indicative of force applied to pedal 74. Motion sensor 72 may generate a signal indicative of the distance between imaging system 10 and table 20. Sensors 68, 70, 72 therefore provide an indication of the position of imaging system 10 or a component thereof.

In accordance with another embodiment of the present teachings, information regarding the position of imaging system 10 may be obtained based on inputs to or outputs from the imaging system 10. In one embodiment, image data output to display 32 or another destination may be captured and read by ECU 56 and the position of imaging system 10 determined based on fiducial markers in the image or through use of optical character recognition or other techniques for reading character data imprinted on the image and indicative of the position of imaging system 10. In addition to the position of imaging system 10, other information associated with the images may be obtained from the image data. This information may include, for example, a time associated with an image such as a start time, stop time or a frame rate for the image. The information may also include an operating mode or the value of an operating parameter (e.g., the amount of radiation generated or a magnification (or zoom) level) for imaging system 10. In other embodiments, control data input to imaging system 10 may be captured and read by ECU and used to determine the position of imaging system 10 and/or other information associated with imaging system 10. For example, an actuation command generated by control pedal 30 may be captured and read by ECU 56 and used to identify the imaging system control (in the case of multiple control inputs) and to determine the beginning and end times of image capture. An output signal from imaging system 10 to a facility's warning light indicative of radiation emission may also be captured and read by ECU 56 and used to determine the beginning and end time of image capture.

In accordance with yet another embodiment of the present teachings, information regarding the position of imaging system 10 and/or other information associated imaging system 10 may be obtained by sensing the activation of imaging system 10 and, in particular, the existence of radiation from emitter 26. Radiation emissions may be detected using a radiation detection sensor such as the XB8816 Series sensor offered for sale by X-Scan Imaging Corporation. ECU 56 may be configured to determine a time associate with the radiation emission responsive to a signal generated by the radiation detector sensor and thereby synchronize signals generated by other sensors such as position sensors 46, 48, 50, 52, 54.

In accordance with yet another embodiment of the present teachings, information regarding the position of imaging system 10 may be obtained by detecting objects, such as anatomical or artificial fiducials, in images generated by system 10 that have a known position within coordinate system 42. To limit interference with the physician's view of the anatomy, these objects may have multiple states whereby the objects are visible in some images and invisible in others or may be generally undetectable to the human eye, but detectable through image processing as described in greater detail in PCT International Publication No. WO 2012/090148 A1, the entire disclosure of which is incorporated herein by reference.

Figure 6:
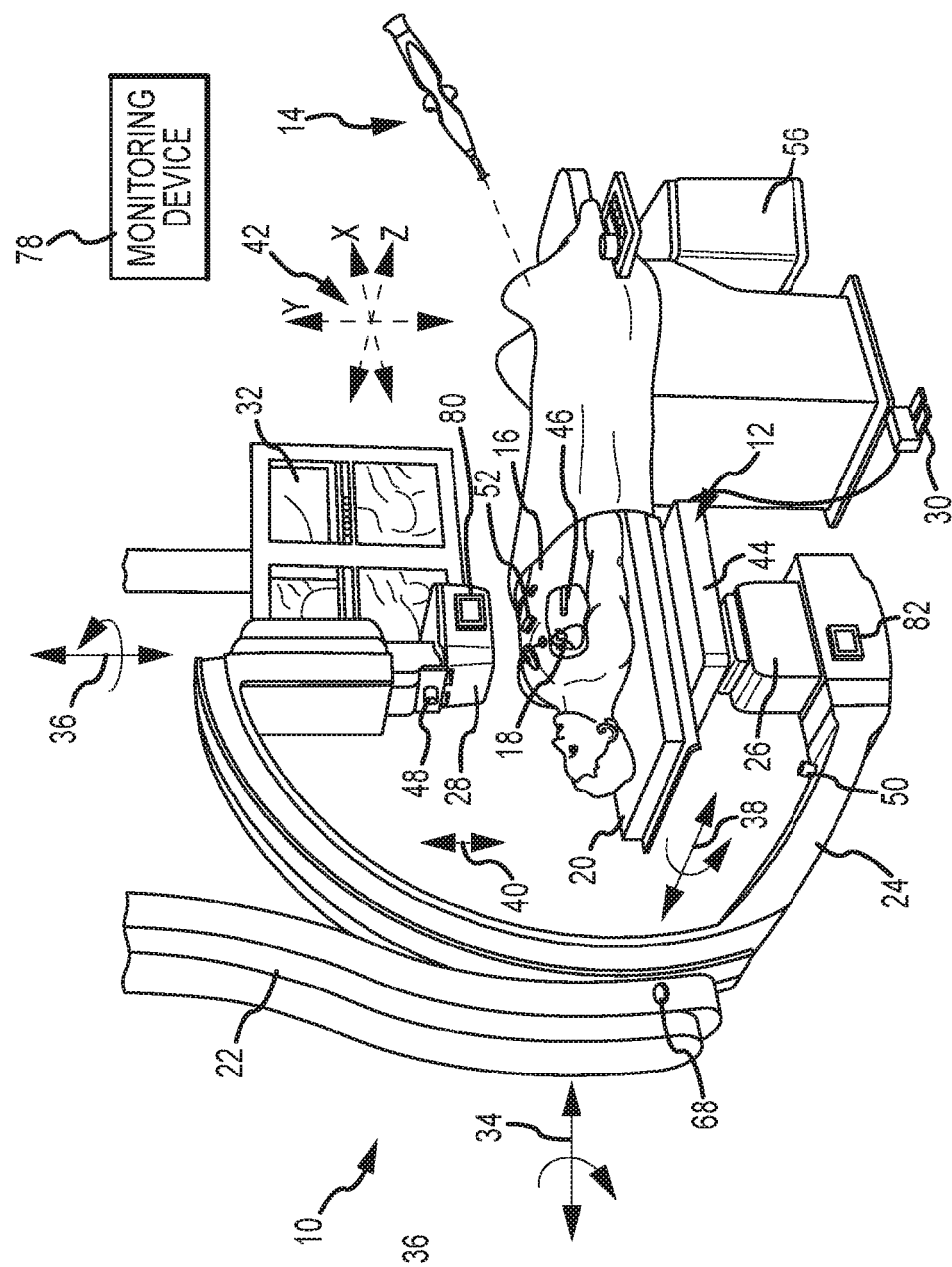
FIG. 6 is a diagrammatic view of a medical device navigation system in accordance with another embodiment of the present teachings.

In accordance with yet another embodiment of the present teachings, information regarding the position of imaging system 10 may be obtained using sensors that remotely monitor movement of imaging system 10. Referring to FIG. 6, a position monitoring device 78 may be positioned remote from imaging system 10 and detect movement of imaging system 10. Device 78 may, for example, comprise a video camera. Images from the camera may be processed by ECU 56 to determine changes in position of imaging system 10. Device 78 may alternatively comprise an ultrasound transducer that generates ultrasonic waves towards imaging system and detects reflection of such waves as an indication of position or an infrared or other optic based sensor that detects reflection of light waves generated by a light emitter. Imaging system 10 may include one or more reflectors 80, 82 or similar devices intended to reflect waves generated by device 78 or another emitter. Thus, a system for navigating a medical device 14 in accordance with one embodiment may include magnetic field generator assembly 44, a position monitoring device 78 remote from imaging system 10, first and second position reference elements such as reflectors 80, 82 or emitters (depending on the composition of position monitoring device 78) and an ECU 56 with at least one of the position reference elements affixed to imaging system 10 and wherein one of assembly 44 or the position reference elements is correlated to a position of emitter 26, another of assembly 44 or the position reference elements is correlated to a position of detector 28 and yet another of assembly 44 or the position reference elements is correlated to a position of body 16, and ECU 56 is configured to determine, responsive to signals received from position sensor 46 on device 14 and device 78, a position of device 14 and a position of emitter 26 or detector 28 within coordinate system 42 and a distance between emitter 26 and detector 28.

Although various embodiments have been disclosed above for obtaining information regarding the position of imaging system 10, it should be understood that elements of multiple embodiments could be used in combination. As but one example, information about the position of the imaging system 10 could be obtained using position sensors 48, 50 and motion sensor 68 (e.g., ECU 56 could separately determine the position of imaging system 10 in response to each sensor and average the values to reduce error).

Referring again to FIG. 1, ECU 56 provides a means for determining the position of sensors 46, 48, 50, 52, 54—and the objects to which sensors 46, 48, 50, 52, 54 are attached—within coordinate system 42. As discussed below, ECU 56 may further provides a means for registering images generated by imaging system 10 in coordinate system 42 and superimposing images of device 14 on such images, a means for comparing the positions of various objects in the EP lab (such as imaging system 10 and generator assembly 44 or body 16 or table 20) to determine potential interference, and/or a means for providing information about the positions of various objects to a physician or other user of system 12. ECU 56 also provides a means for controlling the operation of various components of system 12 including magnetic field generator assembly 44. In embodiments where medical device 14 comprises an electrophysiology or ablation catheter, ECU 56 may also provide a means for controlling device 14 and for determining the geometry of heart 18, electrophysiology characteristics of heart 18 and the position and orientation of device 14 relative to heart 18 and body 16. ECU 56 may also provide a means for generating display signals used to control a display such as display 32. ECU 56 may comprise one or more programmable microprocessors or microcontrollers or may comprise one or more application specific integrated circuits (ASICs). ECU 56 may include a central processing unit (CPU) and an input/output (I/O) interface through which ECU 56 may receive a plurality of input signals including signals generated by sensors 46, 48, 50, 52, 54, and generate a plurality of output signals including those used to control and/or provide data to magnetic field generator assembly 44 and display 32.

In accordance with the present teachings, ECU 56 may be configured with programming instructions from a computer program (i.e., software) to implement a method for navigating a medical device 14 within body 16. The program may be stored in a computer storage medium such as a memory (not shown) that is internal to ECU 56 or external to ECU 56 and may be pre-installed in the memory or obtained from a computer storage medium external to ECU 56 including from various types of portable media (e.g., compact discs, flash drives, etc.) or file servers or other computing devices accessible through a telecommunications network.

Figure 7:
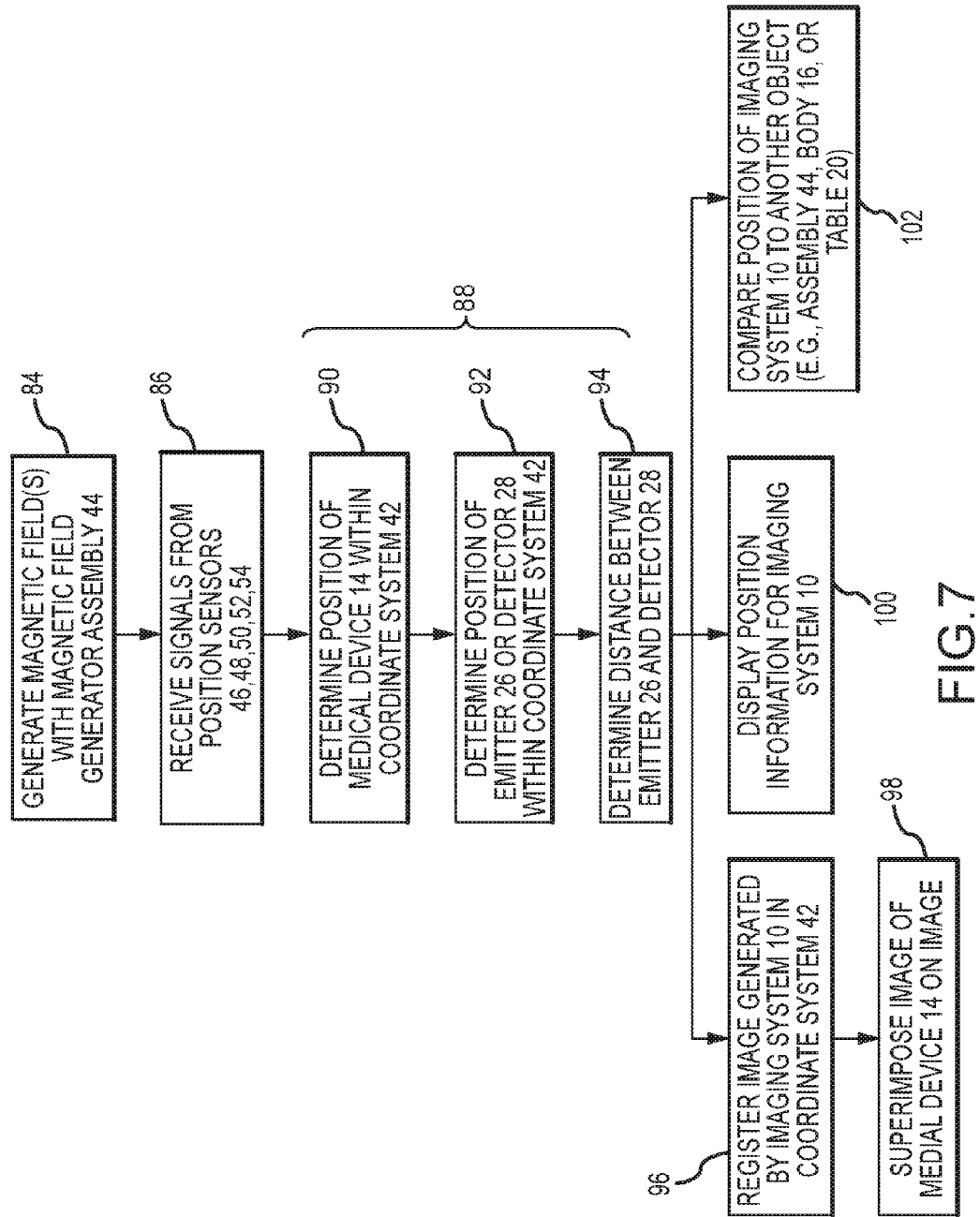
FIG. 7 is a flow chart diagram illustrating methods for navigating a medical device in accordance with several embodiments of the present teachings.

Referring to FIG. 7, an exemplary method for navigating a medical device 14 within body 16 may begin with the step 84 of generating one or more magnetic fields with a magnetic field generator assembly 44 disposed outside of body 16. ECU 56 may generate control signals to magnetic field generator assembly 44 causing generation of the magnetic fields. The method may continue with the step 86 of receiving position signals from one or more of position sensors 46, 48, 50, 52, 54 responsive to the location of sensors 46, 48, 50, 52, 54 within the magnetic fields. The method may continue with the step 88 of determining, responsive to the signals from one or more of sensors 46, 48, 50, 52, 54, the positions of various objects in the electrophysiology lab and within coordinate system 42 and related information. In accordance with one embodiment of the present teachings, step 88 may include the substeps 90, 92, 94 of determining the position of medical device 14, determining the position of at least one of emitter 26 and detector 28 and determining a distance between emitter 26 and detector 28. ECU 56 may determine the positions, in part, by comparing the current value of position signals to a reference value indicative of the origin of coordinate system 56. ECU 56 may determine the position of emitter 26 and/or detector 28 and the distance between emitter 26 and detector 28 using vector-calculus when sensors 48, 50 comprise six degree of freedom sensors because sensors 48, 50 are attached to rigid bodies in detector 28 and emitter 26, respectively. Alternatively, ECU 56 can use neural network algorithms to learn to generate accurate outputs of the position of emitter 26 and/or detector 28 and the distance between emitter 26 and detector 28 responsive to inputs from a group of sensors (e.g., 48, 50, and 54). ECU 56 may be configured to determine the positions despite variation in the position of generator assembly 44 and using various combinations of sensors 48, 50, 52. To account for the various degrees of freedom within the illustrated electrophysiology lab, one of assembly 44 and sensors 48, 50, 52 may be correlated to a position of emitter 26, another of assembly 44 and sensors 48, 50, 52 may be correlated to a position of detector 28 and yet another of assembly 44 and sensors 48, 50, 52 may be correlated to a position of body 16. For example, in the illustrated embodiment, assembly 44 may be correlated to body 16 by virtue of the attachment of assembly 44 and body 16 to table 20, sensor 48 may be correlated to detector 28 and sensor 50 may be correlated to emitter 26. In an alternative embodiment, assembly 44 may be attached, for example, to detector 28 and be correlated with detector 28, while sensor 50 may be correlated to emitter 26 and sensor 52 may be correlated to body 16.

Using information regarding the positions of device 14 and imaging system 10, ECU 56 may be further configured to perform various functions. For example, in one embodiment, ECU 56 may be configured to perform the step 96 of registering an image generated by imaging system 10 in coordinate system 42. Step 96 may include the substep of determining the angle or orientation of arm 24, emitter 26 and/or detector 28. ECU 56 can determine the angle or orientation of arm 24, emitter 26 and/or detector 28 responsive to the position signal generated by sensor 50. Using the angle of orientation and the distance between emitter 26 and detector 28, ECU 56 can register image within coordinate system 42. ECU 56 may further be configured to determine the coordinates in coordinate system 42 of individual pixels within the image. ECU 56 may further be configured to perform the step 98 of superimposing an image of device 14 on the image responsive to the position signal generated by sensor 46. ECU 56 may generate an icon or similar representation of device 14 at a position on the image responsive to the determined coordinates of sensor 46.

In another embodiment in accordance with the present teachings, ECU 56 may be configured to perform the step 100 of displaying positions of one or more of the detector 28 or other imaging system components on a display such as display 32. Basic position information may be represented numerically or graphically to the physician by ECU 56 on display 32 and may be useful to the physician in to, for example, evaluate the impact of positioning commands on imaging system 10.

In another embodiment in accordance with the present teachings, ECU 56 may be configured to perform the step 102 of comparing the position of radiation detector 28 or another component of imaging system 10 with the position of other objects in the EP lab. For example, ECU 56 may compare the position of detector 28 or another component of imaging system 10 with the known location of magnetic field generator assembly 44. In this manner, ECU 56 can determine whether the current position (or a potential change in position) will cause contact or other physical interference between imaging system 10 and assembly 44. ECU 56 can also determine whether the current position (or a potential change in position) will cause the imaging system to distort or otherwise interfere with the magnetic fields generated by assembly 44. ECU 56 can also determine whether the relative positions of imaging system 10 and assembly 44 will interfere with the acquisition of images by imaging system 10 or otherwise decrease the quality of such images.

ECU 56 may also compare the position of detector 28 or another component of imaging system 10 with a position of body 16 and/or table 20. ECU 56 may be configured to determine the position or a change in position of body 16 or table 20 responsive to position signals generated by position sensors 52, 54 affixed to body 16 and table 20. ECU 56 may then compare the position of body 16 and/or table 20 with that of detector 28 or another component of imaging system 10. ECU 56 may use this information to insure a desired alignment between imaging system 10 and body 16 and/or table 20 and/or to prevent physical contact between imaging system 10 and body 16 and/or table 20. For example, if ECU 56 determines that imaging system 10 and body 16 or table 20 are not properly aligned to capture the intended image, ECU 56 can halt image acquisition by imaging system 10, generate a warning to the physician (e.g., an audible noise or a visual warning on display 32) and/or generate a command resulting in movement of imaging system 10 to realign system 10 with body 16 or table 20. Alternatively, if ECU 56 determines that body 16 and/or table 20 is less than a threshold distance from imaging system 10, ECU 56 can issue a warning to the physician (e.g. an audible noise, or a visual warning on display 32) or issue a command resulting in movement of imaging system 10 away from body 16 and/or table 20. ECU 56 may also act to prevent further commanded movements of imaging system 10 in order to prevent imaging system 10 from contacting body 16 and/or table 20 or falling below a threshold distance between imaging system 10 and body 16 and/or table 20. Thus, in at least one embodiment, by using sensors 46, 48, 50, 52 and ECU 56, the system may eliminate or reduce the reliance on mechanical collision detection devices such as microswitches that may create magnetic interference. The threshold distance may comprise a border of a volume (e.g., a box) surrounding the body 16 and/or table 20. The volume may, in some embodiments, be calibrated to the table 20 or particular body 16 of a given patient through pre-procedure movement of sensors 52 and/or 54 to contact various points on the body 16 and/or table 20, respectively, and use of a graphical user interface for the physician to establish the volume. Alternatively, a plurality of sensors 52, 54 disposed on body 16 and/or table 20, respectively, could be used to establish the volume.

Figure 8:
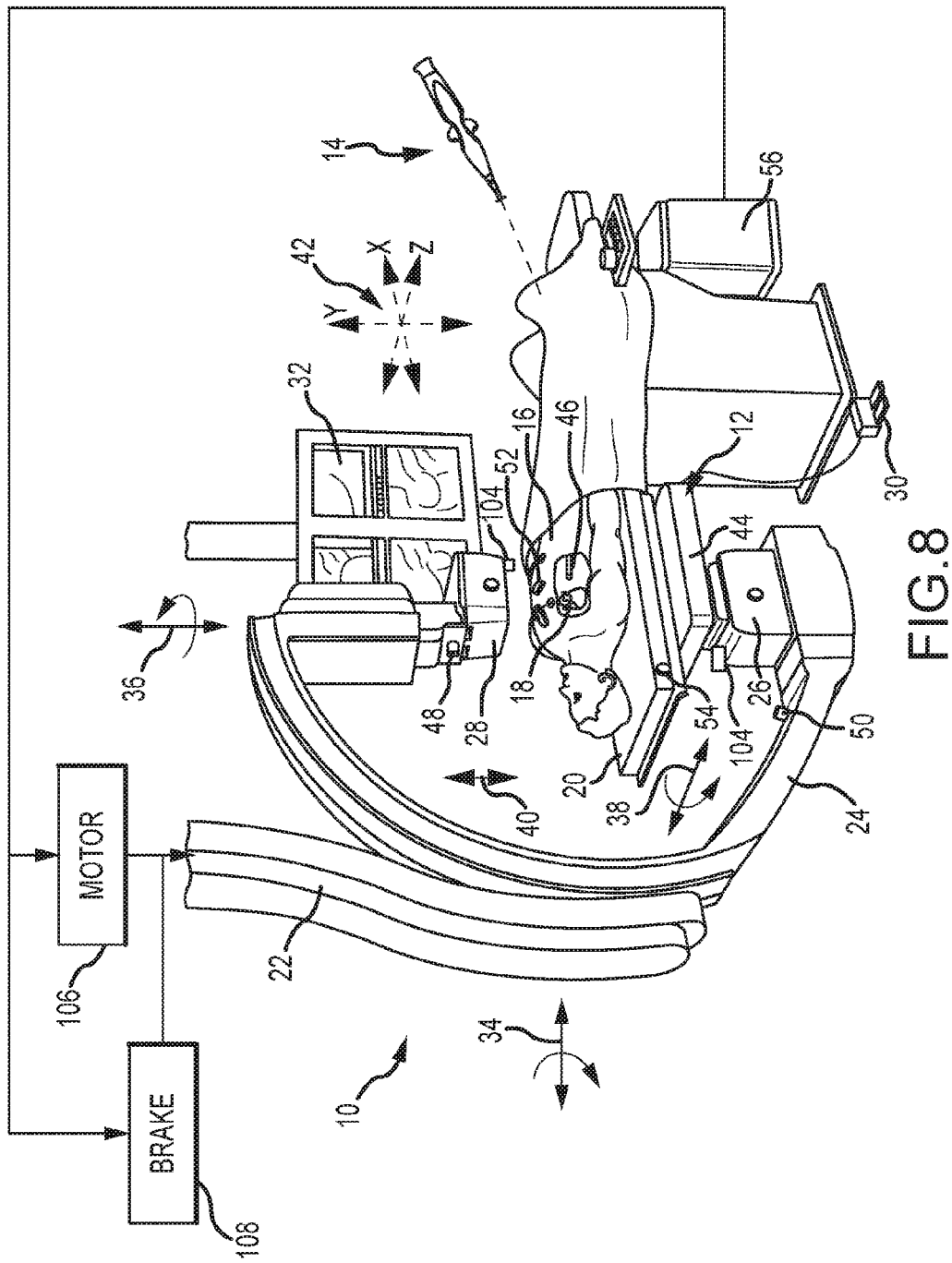
FIG. 8 is a diagrammatic view of a medical device navigation system in accordance with another embodiment of the present teachings.

Referring now to FIG. 8, in various embodiments, an imaging system, such as imaging system 10, may include an imaging system anti-collision feature. Such a feature may be employed to prevent or minimize collision or otherwise undesirable contact between one or more imaging system components and other items in the EP lab, such as for example, body 16, table 20, and/or magnetic field generator assembly 44. Details regarding such an anti-collision feature or features may be found in one or more of the following patents, each of which is hereby incorporated by reference in its entirety: U.S. Pat. No. 5,828,221 (issued 27 Oct. 1998), U.S. Pat. No. 6,408,051 (issued 18 Jun. 2002), U.S. Pat. No. 8,269,176 (issued 18 Sep. 2012), U.S. Pat. No. 4,593,189

(issued 3 Jun. 1986), U.S. Pat. No. 5,072,121 (issued 10 December 1991), U.S. Pat. No. 7,531,807 (issued 12 May 2009), U.S. Pat. No. 7,693,263 (6 Apr. 2010), and U.S. Pat. No. 7,172,340 (issued 6 Feb. 2007). Commercially available anti-collision features include those branded as "SafeMove" available with imaging systems from Siemens AG and "BodyGuard" available with imaging systems from Koninklijke Philips N.V. The anti-collision feature may comprise, for example, force, proximity, and/or capacitive sensors 104. Sensors 104 generate a signal indicative of the distance between components of imaging system 10 and other items in the EP lab, such as for example, body 16, table 20, and/or magnetic field generator assembly 44. The signal can indicate be indicative of the absolute distance or indicate that the distance has fallen below a threshold value. Sensors 104 can transmit signals via a wired or wireless connection to a control unit such as ECU 56 or a dedicated control unit (not shown) for movement of imaging system 10. The control unit generates control signals responsive the signals from sensors 104 to control one or more motors 106 and/or brakes or clutches 108 used in controlling the movement of imaging system along and about axes 34, 36, 38, 40. For example, the control unit may, in response to signals generated by sensors 104, deactivate the motors 106 causing motion of the imaging system components and/or direct brakes 108 to apply mechanical braking force to the same to prevent or inhibit further contact from a component of an imaging system, e.g., system 10, with a patient's body or a patient table, e.g., body 16 or table 20. Alternatively or additionally, such imaging systems may include a programmed, pre-defined spatial envelope of a table's physical dimensions and initial starting position and include the ability to track the table's movement, such that the system may avoid collisions or other undesirable contact by preventing components of the imaging system, such as system 10, from moving undesirably into unnecessary contact with a defined, known object, such as table 20.

In various embodiments, a medical device navigation system, such as navigation system 12 may be configured such that an anti-collision feature of an imaging system, such as imaging system 10 is employed to prevent or minimize undesirable contact between components of the imaging system 10 and components of the navigation system 12. The navigation system 12 may be configured to passively and/or actively cause an anti-collision feature of imaging system 10 to engage. Focusing now on such passive techniques, in various embodiments, one or more components of navigation system 12 may be configured to emulate a patient body 16 or table 20 in such a way that the imaging system 10 does not collide with components of navigation system 12 because the internal anti-collision feature of the imaging system 10 may be activated. This may be achieved passively by emulating the relevant physical characteristic of the body 16 or the table 20 that may be detected by the applicable sensors of the imaging system 10. For example, with an imaging system employing capacitive sensing technology as part of an anti-collision feature, a table-mounted magnetic field generator assembly, such as assembly 44 seen, for example, in FIGS. 1, 5, and 6 and 8, may include a capacitive property that could be detected by the capacitive detector of the imaging system 10. Accordingly, the generator assembly 44 may include a conductive material that may be detected by a capacitive detector of an imaging system. In at least one embodiment, at least part of the magnetic field generator assembly 44 may be built from a conductive material, such as carbon fibers that may also be used in table 20. Additionally or alternatively, at least part of the generator assembly 44 may be painted with a conductive paint and/or covered with a conductive cover, such as a bag or wrap made of a conductive cloth.

Moving to active techniques of engaging an anti-collision feature of an imaging system 10, in various embodiments, navigation system 12 may be configured to actively cause an anti-collision feature to activate. In at least one embodiment, ECU 56 may be configured to send a signal or appropriate electromagnetic wave to imaging system 10 to engage an anti-collision feature such as that described above. For example, positions and dimensions of the applicable components of the imaging system 10 (e.g., the emitter 26 and detector 28) and the applicable components of navigation system 12 (e.g., the generator assembly 44) may be accounted for by ECU 56, as discussed above in relation to step 102 (see FIG. 7). Where collision or other undesirable contact is imminent or already occurring, ECU 56 may cause imaging system 10 to engage an anti-collision feature and/or generate a warning to the physician or other operator of imaging system 10 and/or navigation system 12. In such embodiments, an interface, such as a TCP/IP communication between the imaging system 10 and navigation system 12 may be used to send a relevant message therebetween based on an agreed protocol between the systems. Additionally or alternatively, navigation system 12 and/or imaging system 10 may include one or more designated parts (not shown) that may activate an anti-collision feature by being actuated remotely by ECU 56. For example, with an imaging system employing force sensing technology as part of an anti-collision feature, a designated part may be configured to push on a force sensor and/or other mechanical anti-collision detector of the imaging system 10. Such a designated part may be installed close to each force sensor(s) 104 in the emitter 26 and detector 28 of imaging system 10.

Although several embodiments of a system in accordance with present teachings have been described above with a certain degree of particularity, those skilled in the art could make numerous alterations to the disclosed embodiments without departing from the scope of this disclosure. All directional references (e.g., upper, lower, upward, downward, left, right, leftward, rightward, top, bottom, above, below, vertical, horizontal, clockwise and counterclockwise) are only used for identification purposes to aid the reader's understanding of the disclosed embodiments, and do not create limitations, particularly as to the position, orientation, or use of the disclosed embodiments. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the present teachings as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A system for navigating a medical device relative to a body, comprising:
an electronic control unit (ECU) comprising a processor, the ECU configured to:
receive a device position signal from a device position sensor disposed on the medical device, the device position sensor generating the device position signal responsive to a position of the device position sensor within a magnetic field generated by a magnetic field generator assembly;
receive first and second reference position signals from a first position sensor and a second position sensor, respectively, the first reference position sensor configured to be affixed to an imaging system of a type comprising a structure movable relative to the body and comprising an arm, a radiation emitter coupled to the arm and a radiation detector coupled to the arm and movable relative to the arm, the second reference position sensor configured to be affixed to the imaging system, the first and second reference position signals responsive to positions of the first and second reference position sensors within the magnetic field; and
determine, responsive to the device position sensor and the first and second reference position signals, a device position of the medical device within a first coordinate system; a reference position of one of the radiation detector and the radiation emitter within the first coordinate system; and, a distance between the radiation detector and the radiation emitter.

2. The system of claim 1, wherein the electronic control unit is further configured to correlate:
a position of a first member of the magnetic field generator assembly, the first reference position sensor and the second reference position sensor to a position of the radiation emitter;
a position of a second member of the magnetic field generator assembly, the first reference position sensor and the second reference position sensor to a position of the radiation detector; and
a position of a third member of the magnetic field generator assembly, the first reference position sensor and the second reference position sensor to a position of the body.

3. The system of claim 1, further comprising a radiation detection sensor configured to detect radiation emissions from the imaging system, wherein the electronic control unit is further configured to determine a time associated with the radiation emission responsive to a signal generated by the radiation detection sensor.

4. The system of claim 1, wherein a magnetic field generator assembly is configured to passively engage an anti-collision feature of the imaging system.

5. The system of claim 1, where the electronic control unit is configured to actively engage an anti-collision feature of the imaging system.

6. The system of claim 2, wherein the ECU is further configured to display the reference position on a display.

7. A system for navigating a medical device within a body, the medical device comprising a device position sensor, the system comprising:
a magnetic field generator assembly configured to generate a magnetic field resulting in the production of a device position signal by the device position sensor of the medical device when in the magnetic field, wherein the device position signal is indicative of a position of the device position sensor within the magnetic field; and
wherein the magnetic field generator assembly comprises engagement means for engaging an anti-collision feature of an imaging system.

8. The system of claim 7, wherein the engagement means comprises a passive engagement means.

9. The system of claim 8, wherein the passive engagement means comprises a conductive material.

10. The system of claim 9, wherein the conductive material is configured to emulate physical characteristics of the body.

11. The system of claim 8, wherein the passive engagement means comprises carbon fibers.

12. The system of claim 8, wherein the passive engagement means comprises a conductive paint.

13. The system of claim 8, wherein the passive engagement means comprises a conductive cover.

14. The system of claim 7 further comprising an electronic control unit (ECU), and wherein the engagement means comprises an active engagement means operatively connected to the ECU and configured to send a signal or electromagnetic wave to the anti-collision feature of the imaging system.

15. The system of claim 7 further comprising:
a radiation detection sensor configured to detect radiation emissions from the imaging system and to generate a radiation detection signal; and
an electronic control unit configured to determine a time associated with the radiation emission responsive to the radiation detection signal.

* * * * *